United States Patent [19]
Zajacek et al.

[11] 3,993,685
[45] Nov. 23, 1976

[54] PROCESS FOR THE PRODUCTION OF URETHANES

[75] Inventors: John G. Zajacek, Devon; John J. McCoy, Media, both of Pa.

[73] Assignee: Atlantic Richfield Company, Los Angeles, Calif.

[22] Filed: Oct. 21, 1974

[21] Appl. No.: 516,316

[52] U.S. Cl. .......................... 260/471 C; 260/468 E; 260/479 C; 260/482 B; 260/482 C
[51] Int. Cl.² ........................................ C07C 125/06
[58] Field of Search ........ 260/471 C, 468 B, 479 C, 260/482 B, 482 C, 453 PC

[56] References Cited
UNITED STATES PATENTS

| | | | |
|---|---|---|---|
| 3,338,956 | 8/1967 | Mountfield | 260/471 C |
| 3,344,170 | 9/1967 | Strycker | 260/482 B |
| 3,454,620 | 7/1969 | Gamlen et al. | 260/471 C |
| 3,467,694 | 9/1969 | Hardy et al. | 260/471 C |
| 3,644,462 | 2/1972 | Smith et al. | 260/453 PC |
| 3,845,098 | 10/1974 | Massie et al. | 260/471 C |
| 3,895,054 | 7/1975 | Zajacek et al. | 260/471 C |

*Primary Examiner*—Richard L. Raymond
*Attorney, Agent, or Firm*—Delbert E. McCaslin

[57] ABSTRACT

A method for the production of a urethane by reacting an organic hydroxyl group-containing compound, carbon monoxide and an organic nitro-compound at a suitable pressure and reaction temperature in the presence of a catalyst system consisting of a mixture of a tertiary amine and a platinum group metal or platinum group metal compound.

14 Claims, No Drawings

PROCESS FOR THE PRODUCTION OF URETHANES

BACKGROUND OF THE INVENTION

A number of prior art processes have been proposed for the manufacture of urethanes by reacting hydroxyl group-containing organic compounds, such as alcohols or phenols, with carbon monoxide and certain organic nitro-compounds including the use of catalysts such as certain metal carbonyls, certain complexes of transition metals and noble metal compounds and a Lewis acid.

This invention relates to an improved method for the preparation of urethanes. More particularly, it relates to the preparation of urethanes by reacting an organic nitro-compound, a hydroxyl group-containing compound and carbon monoxide under elevated temperature and pressure conditions in the presence of an effective amount of a catalyst consisting of a mixture of a tertiary organic amine and a platinum group metal or platinum group metal compound.

U.S. Pat. No. 3,338,956 discloses a process for the manufacture of urethanes by reacting a hydroxyl compound, carbon monoxide, and an aliphatic or aromatic nitro-compound at superatmospheric pressures and high temperatures in the presence of a metal carbonyl of elements in groups VIa, VIIa, and VIIIa of the Periodic Table with reaction times ranging from 7 to 18.5 hours.

U.S. Pat. No. 3,454,620 discloses a process for the manufacture of urethanes by reacting an organic compound containing at least one hydroxyl group with carbon monoxide and a nitrogenous organic compound such as nitrobenzene in the presence of a catalyst of complex compound of a platinum group metal and at least one unsaturated hydrocarbon ligand in which the unsaturated system forms a bond with the metal and co-catalyst of a salt of a transition metal.

U.S. Pat. No. 3,467,694 describes a process for preparing a urethane compound by reacting a hydroxy compound, carbon monoxide and an aromatic nitro-compound, at specific molar ratios of carbon monoxide to nitro group, in the presence of a noble metal and a Lewis acid catalyst system. Palladium or rhodium (on-carbon) and the Lewis acid ferric chloride are exemplified and yields of urethane product are not indicated.

The catalyst systems employed in the prior art patents, namely, the metal carbonyls, noble metal/Lewis acid and the platinum group metal/hydrocarbon ligand/transition metal complexes generally require the use of longer reaction times and provide only mediocre yield of urethane product. In addition, the Lewis acid systems present a problem from the standpoint of corrosion, recovery of product and overall handling of reactants.

Many important commercial applications have been developed for the urethane products of this invention, for example, as agricultural chemicals and as chemical intermediates which may be converted to the corresponding isocyanates and alcohols by thermal decomposition or other methods described in the prior art.

SUMMARY OF THE INVENTION

According to the present invention there is provided an improved method for the manufacture of urethanes by reacting an organic nitro-compound with carbon monoxide and an organic hydroxyl group-containing compound which method is carried out at elevated temperatures and pressures.

It has been found that the above-mentioned reaction can be carried out at a faster rate at high conversions of the nitro-compound with excellent yield of urethane products by conducting the reaction in the presence, as catalyst, of high concentrations of a tertiary amine with an effective amount of a platinum group metal or platinum group metal compound.

It is a primary object of this invention to provide an improved method for the preparation of urethanes.

It is another object of this invention to provide a novel catalyst system useful in the direct conversion of organic nitro-compounds to the corresponding urethanes.

It is a further object of this invention to provide an improved method for preparing urethanes such as diethyl toluene-2,4-dicarbamate and diethyl toluene-2,6-dicarbamate,.

These and other objects and advantages of this invention will become apparent from the description of the invention which follows and from the claims.

DESCRIPTION OF THE INVENTION

In accordance with this invention a urethane is produced by reacting an organic compound containing at least one hydroxyl group with carbon monoxide and an aromatic, cycloaliphatic or aliphatic mono- or poly-nitro compound at elevated temperatures and pressures in the presence of a catalyst consisting of a mixture of a tertiary amine and a platinum group metal or platinum group metal compound.

The reaction between the hydroxyl-containing compound, the nitro-compound and carbon monoxide may be carried out in an autoclave or any other high pressure reactor. A general procedure is to change the nitro-compound, the hydroxyl compound and catalyst into the reaction vessel, introduce the proper amount of carbon monoxide, and then heat the mixture to obtain the desired reaction pressure. The reaction can be carried out batchwise or as a continuous process and the other of addition of the reactants may be varied to suit the particular apparatus employed. The reaction products are recovered and treated by any conventional method to effect separation of urethane from unreacted starting material, catalyst, by products, etc.

The hydroxyl group-containing compounds suitable for use in the method of the present invention may be, for example, mono- or polyhydric alcohols containing primary, secondary or tertiary hydroxyl groups as well as mono- and polyhydric phenols. Mixtures of these hydroxy compounds may also be used. The alcohols may be aliphatic or aromatic and may contain other substituents such as halo, amido, alkoxy, tertiary amino, carboxy, cyano, etc., radicals in addition to the hydroxy groups. Substituents, in general, do not interfere with the reaction of the invention. Thus, any hydroxyl-containing compound, or mixtures thereof, is contemplated for use herein, including mono- or polyhydroxy, aromatic or aliphatic, substituted or unsubstituted compounds.

Generally the hydroxyl group-containing compounds conform with one or other of the general formulae $R(OH)_n$ and $R'(OH)_n$ wherein n is 1 or more and preferably from 1 to 3, R is an optionally substituted aliphatic, cycloaliphatic or araliphatic group preferably containing from 1 to 20 carbon atoms, R' is an aromatic group containing one or more benzenoid rings and preferably not more than 3 rings which may be fused or joined by single valency bonds, directly or through bridging groups which may be, for example, oxygen or sulfur atoms or sulfoxide, sulfone or carbonyl groups or alkylene groups in which, if desired, the carbon chain may be interrupted by, for example, oxygen or sulfur atoms, sulfoxide, sulfone, or carbonyl groups, for example methylene, oxymethylene, dimethylene sulfone or dimethylene ketone groups.

The groups R may be alkyl, cycloalkyl, alkylene, cycloalkylene or aralkyl and the main carbon chain may if desired be interrupted, for example, by oxygen or sulfur atoms, sulfoxide, sulfone, carbonyl or carboxylic ester groups. The main chain may bear as substituents, for exmple, alkyl, alkoxy, aryl or aryloxy groups normally containing less than 10 carbon atoms. Especially suitable compounds of the formula $R(OH)_n$ are monohydric alcohols such as methyl, ethyl n-, iso-, sec- and tert-butyl, amyl, hexyl, lauryl, n- and sec-propyl, cetyl, benzyl, chlorobenzyl and methoxy-benzyl alcohols as well as diols such as ethylene glycol, diethylene glycol, propylene glycol and dipropylene glycol, triols such as glycerol, trimethylol propane, hexanetriol, tetrols such as pentaerythritol and the ethers of such polyols providing that at least one OH group remains unetherified. The etherifying groups in such ether alcohols normally contains up to 10 carbon atoms and is preferably an alkyl, cycloalkyl or aralkyl group which may be substituted, for example, a halogeno alkyl group. An especially suitable compound of the formula $R(OH)_n$ is ethanol but other preferred compounds are methanol, propanol, butanol, ethylene glycol, glycerol and trimethylol propane.

The phenolic compounds of the general formula $R(OH)_n$ may carry substituents in the benzenoid rings, for example, alkyl and alkoxy groups containing up to 10 carbon atoms and halogen atoms. Suitable mono and polyhydric phenols include phenol, chlorophenol, methyl, ethyl, butyl an alkyl phenols, catechol, resorcinol, quinol, 4,4'-dihydroxydiphenylmethane, naphthols, chloronaphthols, methyl, ethyl, butyl and octyl naphthols, anthranols, chloroanthranols, methyl, ethyl, butyl and octyl anthranols phenanthrols, chlorophenanthrols, methyl, ethyl, butyl and octyl phenanthrols, pyrogallol, phloroglucinol, hydroxyquinol and the ethers of the polyhydroxyphenols providing at least one OH remains unetherified. The etherifying group in such ethers normally contains up to 10 carbon atoms and is preferably an alkyl, cycloalkyl or aralkyl group which may be substituted, for example, a halogenoalkyl group.

Any organic nitro-compound capable of being converted to urethane may be employed as a reactant in the process of this invention. Aromatic, cycloaliphatic and aliphatic mono- or polynitro compounds, which may be substituted, can be reacted to form the corresponding urethane.

Suitable nitro-compounds containing at least one non-cyclic group in which a nitrogen atom is directly attached to a single carbon atom and through a double bond to oxygen or another nitrogen such as organic nitro, nitroso, azo and azoxy compounds may be used in the method of this invention.

Representative nitro compounds for use in the method include mononitro compounds such as nitrobenzene, alkyl and alkoxy nitrobenzenes wherein the alkyl group contains up to 10 carbon atoms, aryl and aryloxy nitrobenzenes, wherein the aryl group is phenyl, tolyl, naphthyl, xylyl, chlorophenol, chlorotolyl, chloroxylyl or chloronaphthyl, chloronitrobenzenes, dinitro compounds such as dinitrobenzene, alkyl and alkoxy dinitrobenzenes wherein the alkyl group contains up to 10 carbon atoms, aryl and aryloxy dinitrobenzenes, trinitrocompounds such as trinitrobenzene, alkyl and alkoxytrinitrobenzenes, aryl and aryloxytrinitrobenzenes, aryl and aryloxytrinitrobenzenes, the substituents being any of those already mentioned and chlorotrinitrobenzenes as well as similarly substituted mono- and polynitro derivatives of the naphthalene, diphenyl, diphenylmethane, anthracene and phenanthrene series. Substituted or unsubstituted aliphatic nitro compounds such as nitromethane, nitroethane, nitropropane, nitrobutane, 2,2'-dimethyl nitrobutane, nitrocyclopentane, nitrocyclohexane, nitrocyclobutane, 3-methylnitrobutane, nitrooctadecane, 3-nitropropene-1, phenyl nitromethane, p-bromophenyl nitromethane, p-nitrophenyl nitromethane, p-methoxy phenyl nitromethane, dinitroethane, dinitropropane, dinitrobutane, dinitrohexane, dinitrodecane, dinitrocyclohexane, dinitromethylcyclohexane, di-(nitrocyclohexyl)-methane are also suitable. From this group of nitro compounds nitrobenzene, nitrotoluene, dinitrobenzene, dinitrotoluene, trinitrobenzene, trinitrotoluene, mononitronaphthalene, dinitronaphthalene, 4,4'-dinitrodiphenylmethane, nitrobutane, nitrocyclohexane, p-nitrophenylnitromethane, dinitrocyclohexane, dinitromethylcyclohexane, dinitrocyclohexylmethane, are preferred and in particular aromatic nitro compounds especially 2,4- and 2,6-dinitrotoluene and meta and para dinitrobenzenes.

Examples of suitable nitroso compounds are the aromatic nitroso compounds such as nitroso benzene, nitrosotoluene, dinitrosobenzene, dinitrosotoluene and the aliphatic nitroso compounds such as nitrosobutane, nitrosocyclohexane and dinitrosomethylcyclohexane.

Suitable azo compounds have the general formula $R_1-N=N-R_2$, wherein $R_1$ and $R_2$ may be either the same or different substituted or unsubstituted alkyl or aryl groups selected from amongst those already listed in the description of suitable nitro compounds. Azobenzene, nitroazobenzene, chloroazobenzene and alkyl or aryl substituted azobenzene are particularly preferred.

Suitable azoxy compounds have the general formula $$R_1-N=N-R_2$$
$$\uparrow$$
$$O$$

wherein $R_1$ and $R_2$ may be the same or different substituted or unsubstituted alkyl or aryl groups selected from amongst those already listed in the description of suitable nitro compounds. Azoxybenzene, nitroazoxybenzene, chloroazoxybenzene, alkyl and aryl substituted azoxybenzenes are particularly preferred.

The invention includes the use of any mixture of nitro compounds, nitroso compounds, azo or azoxy compounds with any mixture of hydroxy compounds and also the use of compounds containing both functions, i.e., hydroxy-nitro compounds, hydroxynitroso compounds, hydroxyazo and hydroxyazoxy compounds such as 2-hydroxynitroethane, 2-hydroxynitrosoethane, nitrophenols, nitronaphthols, hydroxy azobenzenes and hydroxyazoxybenzene. Mixtures of these nitrogen-containing compounds may also be used.

The process of the invention has been found to proceed most smoothly to give the highest yields when employing nitro compounds. It is accordingly preferred to use nitro compounds rather than nitroso, azo or azoxy compounds.

The catalyst system of this invention is a mixture of at least one tertiary amine compound preferably, the heteroaromatic amines with at least one platinum group metal or platinum group metal compound preferably, the platinum group metal halides and acetates.

The tertiary amines which are suitable for use as components of the catalyst system of this invention include aliphatic, aromatic and heteroaromatic tertiary amines. The amines may be unsubstituted or contain other substituents such as halides, alkyl, aryl, hydroxy, amino, alkylamino, carboxy, etc. The heteroaromatic tertiary amines include those containing between five and six members in the ring, containing only nitrogen of up to 2 nitrogen atoms and carbon in the ring and containing at least two double bonds in the ring.

Representative aliphatic tertiary amines include, for example, triethylamine, tri-n-propylamine, triisopropylamine, tributylamine, triamylamine, 1,1,3,3-tetramethylbutylamine, tridodecylamine, methyldiethylamine, isopropyl dimethylamine, 2 chloro-N,N-diethylethylamine, butyldimethylamine, 3 Cl-N,N-diethylpropylamine, triethanolamine, etc.

Representative aromatic tertiary amines include, for example, N,N-dimethyl aniline, N,N-diethylaniline, triphenyl-amine, benzyldimethylamine, etc.

Representative heteroaromatic tertiary amines include, for example, pyridine, isoquinoline, quinoline, 2-methyl-5-ethylpyridine, 1 methyl pyrole, pyrazole, imidazole, indole, carbazole, 2,6-dimethyl-pyridine, 4-phenylpyridine, 2-bromopyridine, 2-chloropyridine, 2-chloro-4-methylpyridine, 2-methoxypyridine, 2-aminopyridine, 4-dimethylaminopyridine, 4-hydroxypyridine, 4-tertiarybutylpyridine, 2-chloroquinoline, 8-hydroxyquinoline, naphthyridine, benzoquinolines, benzoisoquinolines, purine, pyrazine, 2,6-dimethylpyrazine, quinoxaline, phenazine, etc.

The method of this invention is operated in the presence of high concentrations or an excess of the tertiary amine which then performs as both catalyst and solvent for the reaction system. Although not required, solvents, if desired, which are chemically inert to the components of the reaction system may be employed. Suitable solvents include, for example, aliphatic, cycloaliphatic and aromatic hydrocarbons, such as n-butyl chloride, carbon tetrachloride, mono-, di- and trichlorobenzenes, n-heptane, cyclohexane, benzene, toluene, dichloromethane, perchloroethylene, etc.

The platinum group metals and the compounds thereof which may be employed in the method of this invention are platinum, palladium, ruthenium, rhodium, osmium and iridium. Among the chemical forms of the platinum group metal compounds which can be used are halides, oxides, acetates, sulfates and nitrates, the metal halides and acetates being preferred. Representative platinum group metal compounds include, for example, platinum chloride, platinum oxide, platinum dichloride, platinum iodide, platinum sulfate, platinum bromide, platinum nitrate, platinum acetate, palladium chloride, palladium iodide, palladium acetate, palladium oxide, palladium nitrate, palladium bromide and the corresponding ruthenium, rhodium, osmium and iridium compounds. Mixtures of the platinum group metal compounds as well as mixtures of the metals with the metal compounds may be employed and they may be deployed either with or without a physical support. Generally the platinum group metals are supported which disperses the metals so as to increase surface area. Such supports include alumina, carbon, silica, bentonite and the like.

The reaction is carried out in the presence of a catalytic proportion of the catalyst system. As indicated hereinabove, the tertiary amine component of the catalyst system is utilized in excess amounts and as such also performs as a solvent for the reaction system. Generally the catalyst mixture of the tertiary amine and platinum group metal or platinum group metal compound is used at a ratio of from about 1:1 to 25:1 by weight of tertiary amine to the platinum group metal or platinum group metal compound, but greater or lesser ratios may be employed if desired.

The reaction will proceed with small or trace amounts of the platinum group metal or platinum group metal compound. The upper limit of the metal or metal compound component is governed primarily by cost considerations. The proportions of the catalysts mixture used in the reaction is generally equivalent to between about 0.005 to 0.20 mole of platinum group metal or platinum group metal compound and 5 to 10 mole of tertiary amine per mole of nitro-compound. The median of these ranges are preferred but the preferred range will depend on the equipment and particular conditions used, i.e., the amount of agitation, temperatures, pressures, etc.

An equivalent amount of the hydroxyl group-containing compound for each equivalent of nitro-compound is employed in the reaction. However, if desired, an excess of the hydroxyl group-containing compound may be utilized.

The quantity of carbon monoxide added during the reaction should be sufficient to provide at least 3 moles of carbon monoxide per nitro group. Preferably, however, greater amounts of carbon monoxide are employed, i.e., between about 8 and about 12 moles of carbon monoxide per nitro group in the nitro-compound. In a continuous process wherein a large excess or high carbon monoxide requirements are generally utilized, a suitable recycle of the carbon monoxide may be employed.

For optimum yields, the pressure and temperature should be carefully controlled. The process of this invention is conveniently carried out at pressures in the range of about 400 psig to 10,000 psig and preferably between 600 psig and 2000 psig. The reaction will proceed at temperatures of from about 100° C. to 250° C. It is generally preferred to operate the process at temperatures in the range of 125° C. to 200° C. to avoid side reactions and obtain a convenient rate of reaction. Heating and cooling means may be employed interior and/or exterior of the reactor to maintain the temperature within the desired range.

The reaction time is generally dependent upon the nitro-compound being reacted, temperature, pressure and on the amount of catalyst being charged as well as the type of equipment being employed. Usually between ½ hour and 4 hours at reaction temperatures and pressures are required to obtain the desired degree of reaction but shorter or longer reaction times may be employed. Reaction times will vary dependent on whether the process is continuous or batch. In a continuous process the reaction time may be substantially less than batch reaction time.

The following examples are provided to illustrate the invention in accordance with the principles of this invention but are not to be construed as limiting the invention in anyway except as indicated by the appended claims.

EXAMPLE I 500 ml. titanium autoclave with magnetically actuated stirrer is charged with 10.9 g. of 2,4-dinitrotoluene, 30 ml. of ethyl alcohol, 35 ml. of pyridine and 1g. of palladium chloride. The autoclave is pressurized with carbon monoxide to 1500 psig under a continuous flow of 1000 ml./minute carbon monoxide and heated with agitation at 160° C. for one hour and then cooled, vented and discharged. The reaction product is analyzed by gas-liquid chromatography and shows the conversion of 2,4-din-nitrotoluene to be 100 percent. The yield of diethyl toluene-2,4-dicarbamate is 59.5 percent and a total yield of urethane product of 91.7 percent, i.e., diethyl toluene-2,4-dicarbamate plus ethyl 2-methyl-5-nitrocarbanilate and ethyl 4-methyl-3-nitrocarbanilate.

EXAMPLE II (Comparative)

The procedure of Example I is repeated with the exception that 1 g. of the Lewis acid ferric chloride is substituted for the pyridine. Analysis of the reaction product shows 100 percent conversion of the 2,4-dinitrotoluene. The yield of diethyl toluene-2,4-dicarbamate is 36 percent, ethyl 3-methyl-5-nitrocarbanilate 16 percent, and ethyl 4-methyl-3-nitrocarbanilate 33 percent representing a total yield of urethane product of 85 percent.

EXAMPLE III

A stirred 300 ml. titanium autoclave is charged with 10.9 g. of 2,4-dinitrotoluene, 30 ml. of ethyl alcohol, 35 ml. of pyridine and 1 g. of palladium chloride. The autoclave is pressurized with carbon monoxide to 1000 psig. It is then heated for 65 minutes with agitation to 163° C. when the pressure rose to 1450 psig. The autoclave is cooled, vented, discharged and the reaction product analyzed. Analysis shows a 99 percent conversion of the 2,4-dinitrotoluene. Yield of diethyl toluene-2,4-dicarbamate is 78 percent along with 10 percent 3-amino-4-methyl ethylcarbanilate and 5-amino-2-methyl ethylcarbanilate representing a total yield of urethane product of 88 percent.

EXAMPLE IV

The procedure of Example III is repeated with the exception that 0.5 g. of palladium chloride is employed and the autoclave heated for one hour with agitation to 164° C. with the pressure rising to 1470 psig. which is then cooled, vented and discharged. Analysis of the reaction product shows a 100 percent conversion of the 2,4-dinitrotoluene. Yield of diethyl toluene-2,4-dicarbamate is 46 percent along with 46 percent of ethyl 2-methyl-5-nitrocarbanilate and ethyl 4-methyl-3-nitrocarbanilate representing a total yield of urethane product of 92 percent.

EXAMPLE V

The procedure of Example III is repeated with the exception that 0.25 g. of palladium chloride is employed and the autoclave heated for 40 minutes with agitation to 162° C. with the pressure rising to 1515 psig. Analysis of the reaction product shows a 100 percent conversion of the 2,4-dinitrotoluene. The yield of mono and diurethanes is 55 percent together with 18 percent of a mixture of 2-and 4-methylaniline.

EXAMPLE VI (Comparative)

The procedure of Example I is repeated using 10.9 g. of 2,4-dinitrotoluene, 65 ml. of ethyl alcohol and 1 g. of palladium chloride. No tertiary amine is employed. The conversion of 2,4-dinitrotoluene is only 57 percent giving a 10 percent yield of diethyl toluene-2,4-dicarbamate and 83 percent yield of ethyl methyl nitrocarbanilate isomers.

EXAMPLE VII

The procedure of Example III is repeated substituting an equivalent amount of palladium acetate for the palladium chloride. Conversion of the 2,4-dinitrotoluene is 92 percent. The urethane product is diethyl toluene-2,4-dicarbamate alone with ethyl methyl nitrocarbanilate isomers, amino methyl carbanilate isomers and methyl anilines.

EXAMPLE VIII

The procedure of Example I is repeated using 10 ml. of nitrobenzene, 30 ml. of methyl alcohol, 35 ml. of triethylamine and 1 g. of palladium oxide. The autoclave is heated at 200° C. for one hour. The product is methyl carbanilate.

EXAMPLE IX

The procedure of Example I is repeated using 10 g. 2,4-dinitrochlorobenzene, 78 ml. of ethyl alcohol, 35 ml. triethylamine and 1 g. of palladium chloride. The autoclave is heated at 180° C. for one hour. The product is diethyl-4-chloro-m-benzene-dicarbamate.

EXAMPLE X

The procedure of Example I is repeated using 10.9 g. of 2,4-dinitrotoluene, 60 ml. of ethyl alcohol, 70 ml. of pyridine and 1 g. of palladium acetate. The conversion of 2,4-dinitrotoluene is 83 percent with a 97 percent total yield of urethane product.

EXAMPLE XI

The procedure of Example I is repeated using 10.9 g. of 2,4-dinitrotoluene, 80 ml. of ethyl alcohol, 35 ml. of pyridine and 1 g. of platinum oxide. The product is diethyl toluene-2,4-dicarbamate.

EXAMPLE XII

The procedure of Example III is repeated substituting an equivalent amount of 1,5-dinitronaphthalene for the 2,4-dinitrotoluene. The product is diethyl 1,5-naphthalenedicarbamate.

EXAMPLE XIII

The procedure of Example III is repeated substituting an equivalent amount of allyl alcohol for the ethyl alcohol. The product is diallyl toluene-2,4-dicarbamate.

EXAMPLE XIV

The procedure of Example I is repeated substituting an equivalent amount of rhodium chloride for the palladium chloride an an equivalent amount of ethylene glycol for the ethyl alcohol. The product is diethylene toluene 2,4-dicarbamate.

EXAMPLE XV

The procedure of Example III is repeated substituting an equivalent amount of phenol for the ethyl alcohol and an equivalent amount of 2-chloropyridine for the pyridine. The product is diphenyl toluene-2,4-dicarbamate.

EXAMPLE XVI

The procedure of Example I is repeated substituting an equivalent amount of isoquinoline for the pyridine and an equivalent amount of 2,6-dinitrotoluene for the 2,4-dinitrotoluene. The product is diethyl toluene-2,6-dicarbamate.

EXAMPLE XVII

The procedure of Example I is repeated using 10.9 g. of 2,4-dinitrotoluene, 80 ml. of ethyl alcohol, 70 ml. of pyridine and 4 g. of 10 percent palladium-on-carbon. The autoclave is heated with agitation at 160° C. for one hour. Analysis of the reaction product shows a 73 percent conversion of the 2,4-dinitrotoluene and a 32 percent yield of urethane product.

EXAMPLE XVIII

The procedure of Example I is repeated using 10.9 g. of 2,4-dinitrotoluene, 60 ml. of ethyl alcohol, 70 ml. of pyridine and 1 g. of hydridocarbonyl tris(triphenylphosphine) rhodium (1) [HRh(CO) (Pphenyl$_3$)$_3$]. Analysis of the reaction product shows a yield of 38 percent diethyl toluene-2,4-dicarbamate and a 37 percent yield of mono-urethanes representing a total yield of urethane product of 75 percent.

We claim:

1. A method for the preparation of urethanes which comprises reacting a hydroxyl group-containing organic compound selected from the group consisting of mono- or polyhydric alcohols and mono- or polyhydric phenols with carbon monoxide and an aromatic, cycloaliphatic or aliphatic mono- or poly-nitro compound at a pressure of between 400 psig and 10,000 psig and at a temperature in the range of about 100° C. to 250° C. in the presence of an effective amount of a catalyst of a mixture of between about 0.005 to 0.20 moles of a platinum group metal or platinum group metal compound and between about 5 to 10 moles of an aliphatic, aromatic or heteroaromatic tertiary amine per mole of said nitro compound, the ratio of the tertiary amine to platinum group metal or platinum group metal compound in the catalyst mixture being between about 1:1 to 25:1 by weight.

2. A method according to claim 1 wherein the hydroxyl group-containing compound is selected from the group consisting of ethyl alcohol, methyl alcohol, allyl alcohol, ethylene glycol and phenol.

3. A method according to claim 1 wherein the carbon monoxide is in amounts of at least 3 moles of carbon monoxide per nitro group in the nitro compound.

4. A method according to claim 3 wherein the carbon monoxide is employed in amounts of between about 8 moles and 12 moles of carbon monoxide per nitro group in the nitro compound.

5. A method according to claim 1 wherein the nitro compound is selected from the group consisting of 2,4-dinitrotoluene, 2,6-dinitrotoluene nitrobenzene, 2,4-dinitrochlorobenzene and 1,5- dinitronaphthalene.

6. A method according to claim 1 wherein the pressure is between about 600 psig and 2000 psig and the temperature is in the range of about 125° C. to 200° C.

7. A method according to claim 1 wherein the tertiary amine is selected from the group consisting of pyridine, isoquinoline, triethylamine, and 2-chloropyridine.

8. A method according to claim 1 wherein the platinum group metal compound is a metal halide, oxide, acetate, sulfate, carbonyl or nitrate or mixtures thereof.

9. A method according to claim 8 wherein the platinum group metal compound is selected from the group consisting of palladium chloride, palladium oxide, palladium acetate, platinum oxide, rhodium chloride and hydridocarbonyl tris(triphenylphosphine)rhodium.

10. A method according to claim 1 wherein the tertiary amine is employed in amounts sufficient to perform as a solvent and catalyst for the reaction system.

11. A method for the preparation of diethyl toluene-2,4-dicarbamate which comprises reacting ethyl alcohol with carbon monoxide and 2,4-dinitrotoluene at a pressure of between 600 psig and 200 psig and at a temperature in the range of about 125° C. to 200° C. in the presence of a catalyst consisting of a mixture of a platinum group metal or platinum group metal halide and a heteroaromatic tertiary amine.

12. A method according to claim 11 wherein the platinum group metal halide is palladium chloride and the tertiary amine is pyridine.

13. A method according to claim 11 wherein the catalyst is a mixture of pyridine and palladium metal supported on charcoal.

14. A method according to claim 11 wherein the catalyst is a mixture of pyridine and hydridocarbonyl tris(triphenylphosphine)rhodium.

* * * * *

UNITED STATES PATENT OFFICE
CERTIFICATE OF CORRECTION

PATENT NO. : 3,993,685
DATED : November 23, 1976
INVENTOR(S) : John G. Zajacek and John J. McCoy It is certified that error appears in the above-identified patent and that said Letters Patent are hereby corrected as shown below:

Column 10, Claim 11, line 39 should read:

"pressure of between 600 psig and 2000 psig and at a"

Instead of

"pressure of between 600 psig and 200 psig and at a"

Signed and Sealed this

Fifteenth Day of February 1977

[SEAL]

Attest:

RUTH C. MASON
*Attesting Officer*

C. MARSHALL DANN
*Commissioner of Patents and Trademarks*